(12) United States Patent  
Sugita et al.

(10) Patent No.: US 10,618,894 B2  
(45) Date of Patent: Apr. 14, 2020

(54) PRODUCTION METHOD OF THIAZOLE DERIVATIVE

(71) Applicant: KYOWA HAKKO KIRIN CO., LTD., Chiyoda-ku, Tokyo (JP)

(72) Inventors: Takamasa Sugita, Chiyoda-ku (JP); Arata Yanagisawa, Chiyoda-ku (JP); Iwao Chujo, Chiyoda-ku (JP); Masashi Taga, Chiyoda-ku (JP); Akihiro Mimura, Chiyoda-ku (JP); Atsushi Tada, Chiyoda-ku (JP); Masashi Aoki, Chiyoda-ku (JP)

(73) Assignee: KYOWA KIRIN CO., LTD., Tokyo (JP)

( * ) Notice: Subject to any disclaimer, the term of this patent is extended or adjusted under 35 U.S.C. 154(b) by 0 days.

(21) Appl. No.: 16/246,988

(22) Filed: Jan. 14, 2019

(65) Prior Publication Data

US 2019/0144438 A1    May 16, 2019

Related U.S. Application Data

(62) Division of application No. 15/541,857, filed as application No. PCT/JP2016/051197 on Jan. 8, 2016, now Pat. No. 10,214,523.

(30) Foreign Application Priority Data

Jan. 9, 2015 (JP) ................................. 2015-002964

(51) Int. Cl.
  *C07D 417/14* (2006.01)
  *A61K 31/4439* (2006.01)

(52) U.S. Cl.
  CPC ........ *C07D 417/14* (2013.01); *A61K 31/4439* (2013.01); *C07B 2200/13* (2013.01)

(58) Field of Classification Search
  CPC .................................................. C07D 417/14
  USPC ...................................................... 546/270.7
  See application file for complete search history.

(56) References Cited

U.S. PATENT DOCUMENTS

| | | |
|---|---|---|
| 4,420,478 A | 12/1983 | Heymes et al. |
| 7,718,808 B2 | 5/2010 | Nakajima et al. |
| 7,928,098 B2 | 4/2011 | Uesaka et al. |
| 8,865,731 B2 | 10/2014 | Ouchi et al. |
| 9,249,135 B2 | 2/2016 | Yamada et al. |
| 9,254,283 B2 | 2/2016 | Ikeda et al. |
| 2007/0093516 A1 | 4/2007 | Reaume et al. |
| 2007/0105919 A1 | 5/2007 | Nakajima et al. |
| 2009/0281142 A1 | 11/2009 | Hayakawa et al. |
| 2010/0280023 A1 | 11/2010 | Sugaura et al. |
| 2012/0101101 A1 | 4/2012 | Uesaka et al. |
| 2012/0172362 A1 | 7/2012 | Kase et al. |

FOREIGN PATENT DOCUMENTS

| | | |
|---|---|---|
| WO | 2005/063743 | 7/2005 |
| WO | 2006/011631 | 2/2006 |
| WO | 2006/137527 | 12/2006 |
| WO | 2007/015528 | 2/2007 |
| WO | 2009/145289 | 12/2009 |
| WO | 2010/010908 | 1/2010 |
| WO | 2010/126082 | 11/2010 |

(Continued)

OTHER PUBLICATIONS

Bernstein, "Polymorphism in . . . " p. 115-118, 272. (Year: 2002).*
Davidovich et al., "Detection of polymorphism . . . " Am. Pharm. Rev. 7(1) p. 10, 12, 14, 16, 100.. (Year: 2004).*
Dean "Analytical Chem . . . " p. 10.24-10.26. (Year: 1995).*
Ivanisevic et al. "Use of X-ray . . . " Pharm. Sci. Encycl. p. 1-42.. (Year: 2010).*
Seddon "Pseudopolynnorph " Crystal Growth &amp; design v.4(6) p. 1087 (2 pages from internet). (Year: 2004).*
Rodriguez-Spong et al., "General principles, etc.," Adv. Drug Delivery Reviews 56 241-274. (Year: 2004).*
Kirk-Othmer Encyclopedia of Chemical Technology, 8, pp. 95-147. (Year: 2002).*
Vippagunta et al., "Crystalline Solids", Advanced Drug Delivery Reviews 48 .3-26. (Year: 2001).*
Guillory (in Brittain ed.), "Polymorphism in Pharmaceutical Solids.," NY: Marcel Dekker, Inc., 1-2, 183-226. (Year: 1999).*

(Continued)

*Primary Examiner* — Patricia L Morris
(74) *Attorney, Agent, or Firm* — Venable LLP (57) ABSTRACT

Provided is a production method of a thiazole derivative represented by the formula (I), which has an adenosine $A_{2A}$ receptor antagonistic action and is useful as a therapeutic agent for, for example, Parkinson's disease, sleep disorder, analgesic resistance to opioid, migraine, movement disorder, depression, anxiety disorder and the like. Also provided is a production method of a compound represented by the formula (C), which contains (i) a step of reacting a compound represented by the formula (A) and a compound represented by the formula (B), and the like:

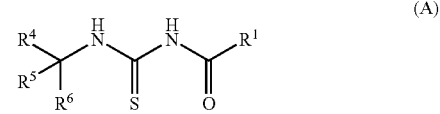

(A)

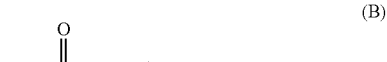

(B)

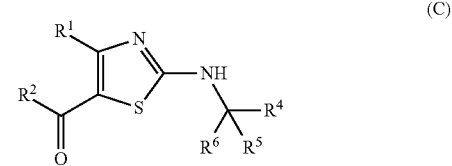

(C)

(wherein $R^1$ represents furyl, $R^4$, $R^5$ and $R^6$ are the same or different and each represents lower alkyl or aryl, $R^2$ represents pyridyl or tetrahydropyranyl, and $X^1$ represents halogen).

8 Claims, 3 Drawing Sheets

(56) References Cited

FOREIGN PATENT DOCUMENTS

| WO | 2011/027805 | 3/2011 |
| WO | 2011/027806 | 3/2011 |
| WO | 2012/027965 | 3/2012 |

OTHER PUBLICATIONS

Braga et al., "Making crystals from . . . " J. Royal Soc. Chem. Commun. p. 3635-3645. (Year: 2005).*

Asahara, et al., Yozai Handbook, 6th Edition, Kodansha Ltd., (1985) ISBN 4-06-1298828(0), 47-51.

Badachikar, et al., "Antiinflammatory, Analgesic & Antibacterial Activities of 4-(2'-Dialkyl/diarylamino-4'-phenyl-5'thiazolylcarbonyl)-3-arylsydnones", Indian Journal of Chemistry, vol. 25B, Issue 4 (1986) 444-46.

Brindley, et al., "N'-Substituted N-Acyl- and N-Imidoyl-thioureas: Preparation and Conversion of N', N'-Disubstituted Compounds into 2-(N,N-Disubstituted Amino)thizone-5-yl Ketones", J. Chem. Soc. Perkin Trans. I (1987) 1153-58.

Friot, et al., "2,4-diamino-1-thia-3-azabutadienes, Intermediates in Heterocyclic Synthesis", Phosphorus, Sulfur, and Silicon and the Related Elements, vol. 156 (2000) 135-49.

Liebscher, et al., "A New Variant for the Synthesis of Substituted 2-Aminothizoles" Z. Chem., vol. 14, Issue 12 (1974) 470-71 (English Translation).

Rajapapp, et al., "A Novel Synthesis of Thiazoles: Part II—Synthesis of 2-Amino-5-nitrothiazoles by Direct Ring closure Reactions", Indian Journal of Chemistry, vol. 16B (1978) 749-51.

Rajapapp, et al., "A General Synthesis of Thiazoles. Part 3. Comparative Evaluation of Different Functionalised Thioureas as Precursors", J.C.S. Perkin I (1979) 1762-64.

Rajapapp, et al., "A Novel Synthesis of Thiazoles", Indian J. Chem., vol. 8 (1970) 1145-46.

* cited by examiner

PRODUCTION METHOD OF THIAZOLE DERIVATIVE

TECHNICAL FIELD

The present invention relates to a production method of a thiazole derivative useful as an adenosine $A_{2A}$ receptor antagonist, a crystal of the thiazole derivative or a monohydrate thereof, and the like.

BACKGROUND ART

It is known that a thiazole derivative represented by the following formula (I) or a pharmaceutically acceptable salt thereof has an adenosine $A_{2A}$ receptor antagonistic action, and is useful as a therapeutic drug for, for example, Parkinson's disease (see patent documents 1 and 2). In addition, a thiazole derivative useful as a therapeutic agent for sleep disorder, analgesic resistance to opioid, migraine, movement disorder, depression, anxiety disorder and the like is known (see patent documents 3, 4, 5, 6, 7 and 8). As these thiazole derivatives, compounds represented by the following formulas (IA), (IB), (IC), (ID) and the like, and the like are specifically known (see patent documents 1, 3, 4, 5, 6, 7 and 8).

(I)

(IA)

(IB)

(IC)

(ID)

(wherein $R^1$ represents furyl, $R^2$ represents pyridyl or tetrahydropyranyl, $R^3$ represents aryl, aralkyl, an aromatic heterocyclic group, aromatic heterocyclylalkyl, aliphatic heterocyclylalkyl or tetrahydropyranyloxy, or these groups substituted by 1 to 3 substituents selected from the group consisting of halogen; lower alkyl optionally substituted by lower alkoxy or morpholino; lower alkoxy; lower alkanoyl; and vinyl)

As production methods of these thiazole derivatives, the following three production methods (Schemes 1-3) are known (see patent document 1).

Scheme 1

(wherein R¹⁰ represents furyl or the like, Hal represents halogen, Ph represents phenyl, R¹² represents as defined above for R² or the like, and R¹¹ represents as defined above for R³ or the like)

(wherein R¹⁰, R¹¹ and R¹² are each as defined above)

Other than the above, for example, a method including reacting α-halomethyl ketone and an N-(aminomethylene) thiourea derivative (see non-patent documents 1-4), a method including reacting α-halomethyl ketone and an N-acyl-thiourea derivative (see non-patent documents 3-6) and the like are also known.

More specifically, the compounds represented by the above-mentioned formulas (IA), (IB), (IC) and (ID) are described in patent document 1 as Examples 504, 508, 557 and 253.

DOCUMENT LIST

Patent Documents patent document 1: WO 2005/063743
patent document 2: WO 2006/137527
patent document 3: WO 2007/015528
patent document 4: WO 2009/145289
patent document 5: WO 2010/010908
patent document 6: WO 2010/126082
patent document 7: WO 2011/027805
patent document 8: WO 2011/027806

Non-Patent Documents non-patent document 1: Indian Journal of Chemistry, 1970, vol. 8, p. 1145 non-patent document 2: Indian Journal of Chemistry, 1978, vol. 16B, p. 749
non-patent document 3: Journal of Chemical Society, Perkin Transactions I, 1979, p. 1762
non-patent document 4: Journal of Chemical Society, Perkin Transactions I, 1987, p. 1153
non-patent document 5: Zeitschrift für Chemie, 1974, vol. 14, p. 470
non-patent document 6: Indian Journal of Chemistry, 1986, vol. 25B, p. 446

SUMMARY OF THE INVENTION

Problems to be Solved by the Invention

An object of the present invention is to provide an industrial production method of a compound represented by the formula (I), which has an adenosine $A_{2A}$ receptor antagonistic action and is useful as a therapeutic agent for, for example, Parkinson's disease, sleep disorder, analgesic resistance to opioid, migraine, movement disorder, depression, anxiety disorder and the like, and the like. Also, the object includes provision of a crystal of a compound represented by the formula (IA) or a monohydrate thereof, and a production method thereof, and the like.

Means of Solving the Problems

The present invention relates to the following (1)-(31).
(1) A production method of a compound represented by the formula (C), comprising (i) a step of reacting a compound represented by the formula (A) and a compound represented by the formula (B):

(wherein $R^1$ represents furyl, $R^4$, $R^5$ and $R^6$ are the same or different and each represents lower alkyl or aryl, $R^2$ represents pyridyl or tetrahydropyranyl, and $X^1$ represents halogen).
(2) The production method according to (1), wherein $X^1$ is a chlorine atom, a bromine atom or an iodine atom.
(3) The production method according to (1), wherein $X^1$ is a bromine atom.
(4) The production method according to any of (1)-(3), wherein $R^4$, $R^5$ and $R^6$ are each methyl.
(5) The production method according to any of (1)-(4), wherein $R^1$ is 2-furyl.
(6) A production method of a compound represented by the formula (I) comprising the step described in any of (1)-(5):

(wherein $R^1$ and $R^2$ are each as defined above, $R^3$ represents aryl, aralkyl, an aromatic heterocyclic group, aromatic heterocyclylalkyl, aliphatic heterocyclylalkyl or tetrahydropyranyloxy, or these groups substituted by 1 to 3 substituents selected from the group consisting of halogen; lower alkyl optionally substituted by lower alkoxy or morpholino; lower alkoxy; lower alkanoyl; and vinyl).
(7) The production method according to (6), further comprising (ii) a step of obtaining a compound represented by the formula (D) by treating a compound represented by the formula (C) with an acid:

(wherein $R^1$, $R^2$, $R^4$, $R^5$ and $R^6$ are each as defined above), and (iii) a step of obtaining a compound represented by the formula (I) by reacting a compound represented by the formula (D) and a compound represented by the formula (E):

(wherein Y represents halogen or hydroxy, and $R^2$, $R^2$ and $R^3$ are each as defined above).
(8) The production method according to (7), wherein the acid in step (ii) is hydrochloric acid or trifluoroacetic acid.

(9) The production method according to (7) or (8), wherein Y is hydroxy.
(10) The production method according to (9), wherein the reaction in step (iii) is performed in the presence of 1,3-dicyclohexylcarbodiimide (DCC), 1-ethyl-3-(3-dimethylaminopropyl)carbodiimide hydrochloride (EDC), 1,1'-carbonyldiimidazole (CDI) or propylphosphonic anhydride (T3P).
(11) The production method according to (9), wherein the reaction in step (iii) is performed in the presence of CDI.
(12) The production method according to any of (1)-(11), wherein $R^2$ is 4-tetrahydropyranyl.
(13) The production method according to any of (6)-(12), wherein $R^3$ is 2-methylpyridin-5-yl, 2-methylpyrimidin-5-yl, 5,6-dihydro-2H-pyridylmethyl or 4-tetrahydropyranyloxy.
(14) The production method according to any of (6)-(12), wherein $R^3$ is 2-methylpyridin-5-yl.
(15) The production method according to any of (6)-(11), wherein $R^1$ is 2-furyl, $R^2$ is 4-tetrahydropyranyl, and $R^3$ is 2-methylpyridin-5-yl.
(16) A production method of a compound represented by the formula (A), comprising a step of reacting a compound represented by the formula (P), a compound represented by the formula (Q) and a thiocyanate salt:

(wherein $X^2$ represents halogen, and $R^1$, $R^4$, $R^5$ and $R^6$ are each as defined above).
(17) The production method according to (16), wherein the thiocyanate salt is sodium thiocyanate or potassium thiocyanate.
(18) The production method according to (16) or (17), wherein $R^1$ is 2-furyl, and $R^4$, $R^5$ and $R^6$ are each methyl.
(19) The production method according to any of (16)-(18), wherein the reaction is performed in tetrahydrofuran (THF).
(20) A crystal of a compound represented by the formula (IA), wherein the compound is a monohydrate:

(21) The crystal according to (20), which has peaks at 8.1° and 12.0° for the angles of diffraction (2θ±0.2°) as determined by powder X-ray diffraction.
(22) The crystal according to (20) or (21), which has peaks at 16.3°, 21.8° and 23.0° for the angles of diffraction (2θ±0.2°) as determined by powder X-ray diffraction.
(23) The crystal according to any of (20)-(22), which has peaks at 14.7°, 21.1°, 24.4°, 24.7° and 28.3° for the angles of diffraction (2θ±0.2°) as determined by powder X-ray diffraction.
(24) A crystal of a compound represented by the formula (IA), wherein the compound is an anhydride:

(25) The crystal according to (24), which has peaks at 8.3° and 19.1° for the angles of diffraction (2θ±0.2°) as determined by powder X-ray diffraction.
(26) The crystal according to (24) or (25), which has peaks at 21.2°, 23.8° and 27.0° for the angles of diffraction (2θ±0.2°) as determined by powder X-ray diffraction.
(27) The crystal according to any of (24)-(26), which has peaks at 12.6°, 16.5°, 19.5°, 20.8° and 22.4° for the angles of diffraction (2θ±0.2°) as determined by powder X-ray diffraction.
(28) A production method of the crystal described in any of (20)-(23), comprising a step of crystallizing a compound represented by the formula (IA) from acetone-water.
(29) A production method of the crystal described in any of (24)-(27), comprising a step of crystallizing a compound represented by the formula (IA) from isobutyl alcohol.
(30) The production method according to (28) or (29), wherein the compound represented by the formula (IA) to be used as a starting material is monohydrate.
(31) The production method according to any of (28)-(30), wherein the compound represented by the formula (IA) to be used as a starting material is a compound obtained by the production method described in any of (6)-(15).

Effect of the Invention

According to the present invention, a production method of a compound represented by the formula (I), which has an adenosine $A_{2A}$ receptor antagonistic action and is useful as a therapeutic agent for, for example, Parkinson's disease, sleep disorder, analgesic resistance to opioid, migraine, movement disorder, depression, anxiety disorder and the like, a production method of a compound represented by the formula (C), which is useful as an production intermediate for a compound represented by the formula (I), a crystal of a compound represented by the formula (IA) or a monohydrate thereof and a production method thereof and the like are provided. The production methods of the present invention are useful as industrial production methods of a drug substance of a pharmaceutical product. In addition, a crystal of a compound represented by the formula (IA) or a monohydrate thereof of the present invention is useful as a drug substance of a pharmaceutical product.

DETAILED DESCRIPTION OF THE INVENTION

In the following, a compound represented by the formula (I) is referred to as compound I. The same applies to the compounds of other formula numbers.

In the definition of each group in the formulas (I), (A), (B), (C), (E), (P) and (Q):

Examples of the lower alkyl, and the lower alkyl moiety of the lower alkoxy and the lower alkanoyl include linear or branched alkyl having 1-10 carbon atoms, and more specific examples thereof include methyl, ethyl, propyl, isopropyl, butyl, isobutyl, sec-butyl, tert-butyl, pentyl, isopentyl, neopentyl, hexyl, heptyl, octyl, nonyl, decyl and the like.

Examples of the aralkyl include aralkyl having 7-16 carbon atoms, and more specific examples thereof include benzyl, phenethyl, phenylpropyl, phenylbutyl, phenylpentyl, phenylhexyl, phenylheptyl, phenyloctyl, phenylnonyl, phenyldecyl, naphthylmethyl, naphthylethyl, naphthylpropyl, naphthylbutyl, naphthylpentyl, naphthylhexyl, anthrylmethyl, anthrylethyl and the like.

Examples of the aryl include aryl having 6-14 carbon atoms, and more specific examples thereof include phenyl, naphthyl, azulenyl, anthryl and the like.

Examples of the aromatic heterocyclic group include a 5-membered or 6-membered monocyclic aromatic heterocyclic group containing at least one atom selected from a nitrogen atom, an oxygen atom and a sulfur atom, a bicyclic or tricyclic fused aromatic heterocyclic group wherein 3- to 8-membered rings are fused, which contains at least one atom selected from a nitrogen atom, an oxygen atom and a sulfur atom, and the like, and more specific examples thereof include furyl, thienyl, pyrrolyl, imidazolyl, pyrazolyl, oxazolyl, isoxazolyl, oxadiazolyl, triazolyl, isothiazolyl, thiadiazolyl, triazolyl, tetrazolyl, pyridyl, pyridazinyl, pyrimidinyl, pyrazinyl, triazinyl, benzofuranyl, benzothiophenyl, benzoxazolyl, benzothiazolyl, isoindolyl, indolyl, indazolyl, benzimidazolyl, benzotriazolyl, oxazolopyrimidinyl, thiazolopyrimidinyl, pyrrolopyridinyl, pyrrolopyrimidinyl, imidazopyridinyl, purinyl, quinolinyl, isoquinolinyl, cinnolinyl, phthalazinyl, quinazolinyl, quinoxalinyl, naphthyridinyl, furo[2,3-b]pyridyl, 6,7-dihydro-5H-cyclopenta[b]pyridyl, 7,8-dihydro-5H-pyrano[4,3-b]pyridyl, 7,8-dihydro-5H-thiopyrano[4,3-b]pyridyl and the like.

Examples of the aromatic heterocyclylalkyl include a group wherein an aromatic heterocyclic group is bonded to alkylene. Examples of the aromatic heterocyclic group include the groups recited as examples of the above-mentioned aromatic heterocyclic group, examples of the alkylene include alkylene having 1-10 carbon atoms, and more specific examples thereof include methylene, ethylene, trimethylene, propylene, tetramethylene, pentamethylene, hexamethylene, heptamethylene, octamethylene, nonamethylene, decamethylene and the like. More specific examples of aromatic heterocyclylalkyl include pyrrolylmethyl, pyrrolylethyl, thiazolylmethyl, pyridylmethyl, pyridylethyl, pyrimidinylmethyl, pyrimidinylethyl, indolylmethyl, benzoimidazolylmethyl and the like.

Examples of the aliphatic heterocyclylalkyl include a group wherein an aliphatic heterocyclic group is bonded to alkylene. Examples of the aliphatic heterocyclic group include a 5-membered or 6-membered monocyclic aliphatic heterocyclic group containing at least one atom selected from a nitrogen atom, an oxygen atom and a sulfur atom, a bicyclic or tricyclic fused aliphatic heterocyclic group wherein 3- to 8-membered rings are fused, which contains at least one atom selected from a nitrogen atom, an oxygen atom and a sulfur atom, and the like, and more specific examples thereof include aziridinyl, azetidinyl, pyrrolidinyl, piperidino, piperidinyl, azepanyl, 1,2,5,6-tetrahydropyridyl, imidazolidinyl, pyrazolidinyl, piperazinyl, homopiperazinyl, pyrazolinyl, oxiranyl, tetrahydrofuranyl, tetrahydro-2H-pyranyl, 5,6-dihydro-2H-pyranyl, 5,6-dihydro-2H-pyridyl, oxazolidinyl, morpholino, morpholinyl, thioxazolidinyl, thiomorpholinyl, 2H-oxazolyl, 2H-thioxazolyl, dihydroindolyl, dihydroisoindolyl, dihydrobenzofuranyl, benzoimidazolidinyl, dihydrobenzooxazolyl, dihydrobenzothioxazolyl, benzodioxolinyl, tetrahydroquinolyl, tetrahydroisoquinolyl, dihydro-2H-chromanyl, dihydro-1H-chromanyl, dihydro-2H-thiochromanyl, dihydro-1H-thiochromanyl, tetrahydroquinoxalinyl, tetrahydroquinazolinyl, dihydrobenzodioxanyl and the like. Examples of the alkylene include alkylene having 1-10 carbon atoms, and more specific examples thereof include methylene, ethylene, trimethylene, propylene, tetramethylene, pentamethylene, hexamethylene, heptamethylene, octamethylene, nonamethylene, decamethylene and the like. More specific examples of the aliphatic heterocyclylalkyl include 5,6-dihydro-2H-pyridylmethyl, 5,6-dihydro-2H-pyridylethyl, tetrahydro-2H-pyranylmethyl, 5,6-dihydro-2H-pyranylmethyl, 5,6-dihydro-2H-pyranylethyl, morpholinomethyl, morpholinoethyl, piperazinylmethyl, oxazolidinylmethyl and the like.

Halogen means each atom of fluorine, chlorine, bromine, iodine.

The production method of compound I (Scheme described below) is specifically explained below.

(wherein M represents a metal atom such as sodium, potassium and the like, and $R^1$, $R^2$, $R^3$, $R^4$, $R^5$, $R^6$, $X^1$, $X^2$ and Y are each as defined above)

Step 1

Compound A can be obtained by reacting compound P, compound Q and a thiocyanate salt in a suitable solvent. These three reagents (compound P, compound Q and thiocyanate salt) may be reacted simultaneously, or respective reagents can also be reacted sequentially in an appropriate order. Preferably, compound A can be obtained by reacting a thiocyanate salt and compound P in a suitable solvent, and then adding compound Q to the obtained reaction mixture to allow for reaction, according to the method described in, for example, J. C. S. Perkin I, 1153 (1987) and the like.

While the amount of each reagent to be used is not particularly limited, it is, for example, preferably 0.8-1.5 equivalents, more preferably 0.9-1.2 equivalents, of compound Q, and preferably 0.8-1.5 equivalents, more preferably 0.9-1.2 equivalents, of thiocyanate salt, both relative to compound P.

Examples of the thiocyanate salt include sodium thiocyanate, potassium thiocyanate and the like, preferably sodium thiocyanate.

While the solvent is not particularly limited, for example, aliphatic hydrocarbon such as pentane, hexane, heptane, cyclohexane and the like; aromatic hydrocarbon such as toluene, xylene and the like; halogenated hydrocarbon such as dichloromethane, chloroform, dichloroethane and the like; polar solvents such as acetonitrile, dimethyl sulfoxide (DMSO), N,N-dimethylformamide (DMF), N,N-dimethylacetamide (DMA), N-methyl-2-pyrrolidone (NMP), 1,3-dimethyl-2-imidazolidinone (DMI) and the like; ethers such as dioxane, THF, diethyl ether, cyclopentyl methyl ether, 1,2-dimethoxyethane (DME), ethylene glycol dimethyl ether and the like; esters such as methyl acetate, ethyl acetate, isopropyl acetate and the like, and the like. These may be used alone or as a mixture thereof.

Preferred are THF and the like. The amount of the solvent to be used is not particularly limited and, for example, 1-50 volume/weight (v/w) is used relative to compound P.

The reaction is performed at a temperature of preferably between −10° C. and 150° C., more preferably 0° C. and 100° C., generally for 5 min-72 hr.

Compound P and compound Q can be obtained as commercially available products.

Step 2 Compound C can be obtained by reacting compound A and compound B.

Compound B is used in preferably 0.1-5 equivalents, more preferably 0.5-2 equivalents, even more preferably 0.9-1.3 equivalents, relative to compound A.

While the reaction can also be performed without solvent, it is preferably performed in a solvent. Examples of the solvent include aliphatic hydrocarbon such as pentane, hexane, heptane, cyclohexane and the like; aromatic hydrocarbon such as toluene, xylene and the like; halogenated hydrocarbon such as dichloromethane, chloroform, dichloroethane and the like; polar solvents such as acetonitrile, DMSO, DMF, DMA, NMP, DMI and the like; ethers such as dioxane, THF, diethyl ether, cyclopentyl methyl ether, DME, ethylene glycol dimethyl ether and the like; esters such as methyl acetate, ethyl acetate, isopropyl acetate and the like; alcohols such as methanol, ethanol, propanol, 2-propanol and the like; water and the like. These may be used alone or as a mixture thereof. Preferred are polar solvents such as DMF, DMA, NMP, DMI and the like. While the amount of the solvent to be used is not particularly limited, for example, it is used at 0.5-20 v/w relative to compound A.

The reaction is performed at a temperature of preferably between −50° C. and the boiling point of the solvent to be used, more preferably a temperature between 10° C. and 70° C., even more preferably between 30° C. and 50° C., for generally 5 min-100 hr.

In this step, when a sterically hindered group, for example, tert-butyl, 1,1-dimethylpropyl, 1-methyl-1-phenylethyl, trityl and the like is present as a substituent —$CR^4R^5R^6$ on one nitrogen atom of compound A, a desired thiazole ring can be selectively produced (compound C is selectively obtained rather than a compound represented by the following formula C1):

(wherein $R^1$, $R^2$, $R^4$, $R^5$ and $R^6$ are each as defined above)

Also, when a suitable polar solvent such as DMF, DMA, NMP, DMI and the like is used, produced compound C can be precipitated as a solid by adding water to the reaction mixture after completion of the reaction, whereby compound C can be obtained by a convenient operation.

Furthermore, compound C is sometimes obtained in the form of a salt containing X. Specifically, for example, when X is a chlorine atom, hydrochloride can be obtained, and when X is a bromine atom, hydrobromide and the like can be obtained.

Compound B can be obtained as a commercially available product, or according to a known method (for example, Organic Synthesis, IV, 193 (1988) and the like). When a commercially available product of compound B is used, it is used after purification if necessary.

Step 3

Compound D can be obtained by treating compound C with an acid without solvent or in a solvent. The treatment is performed preferably at a temperature between −80° C. and the boiling point of the acid or solvent to be used, more preferably at a temperature between 10° C. and 100° C., for generally 1 min-100 hr, preferably 5 min-24 hr. If necessary, a cation scavenger such as anisole and the like is added. The cation scavenger is used in preferably 0.5 equivalent—large excess, more preferably 1-50 equivalents, relative to compound C.

Examples of the acid include hydrogen halides such as hydrochloric acid, hydrobromic acid, hydroiodic acid and the like; sulfonic acids such as methanesulfonic acid, trifluoromethanesulfonic acid, benzenesulfonic acid, paratoluenesulfonic acid and the like; carboxylic acids such as acetic acid, propionic acid, trichloroacetic acid, trifluoroacetic acid, benzoic acid, methylbenzoic acid, trichlorobenzoic acid, trifluorobenzoic acid, pentafluorobenzoic acid and the like; sulfuric acid; nitric acid and the like, preferably hydrochloric acid, trifluoroacetic acid and the like, and it is used in preferably 0.5-200 equivalents, more preferably 1-50 equivalents, relative to compound C.

Examples of the solvent include aliphatic hydrocarbons such as pentane, hexane, heptane, cyclohexane and the like; aromatic hydrocarbons such as toluene, xylene and the like; halogenated hydrocarbons such as dichloromethane, chloroform, dichloroethane and the like; polar solvents such as acetonitrile, DMSO, DMF, DMA, NMP, DMI and the like; ethers such as dioxane, THF, diethyl ether, cyclopentyl methyl ether, DME, ethylene glycol dimethyl ether and the like; esters such as methyl acetate, ethyl acetate, isopropyl acetate and the like; alcohols such as methanol, ethanol, propanol, 2-propanol and the like; water and the like, preferably toluene, dioxane, water and the like. These are used alone or as a mixture thereof. While the amount of the solvent to be used is not particularly limited, for example, it is used in 0.5-20 v/w relative to compound A.

More preferably, for example, compound D can be conveniently obtained in a high yield by treating compound C in 3-12 mol/L hydrochloric acid at a temperature between 50° C. and 100° C.

After the above-mentioned treatment, compound D can be easily obtained from the reaction mixture by, for example, neutralizing the reaction mixture with a suitable base such as lithium hydroxide, sodium hydroxide, potassium hydroxide, potassium carbonate, sodium carbonate and the like. Compound D can also be easily obtained by performing the treatment while evaporating a by-produced low boiling point compound, acid and the like by using a Dean-Stark trap and the like. To evaporate the by-produced low boiling point compound, acid and the like, it is also effective to perform the reaction under reduced pressure.

Step 4

Compound I can be obtained by reacting compound D and compound E.

(1) When Y in compound E is hydroxy, compound I can be obtained by reacting compound D and compound E in a solvent, in the presence of a condensing agent and, if necessary, in the presence of an additive.

Compound E is preferably used in 0.8-5 equivalents, more preferably 1-2 equivalents, relative to compound D.

Examples of the condensing agent include 1,3-dicyclohexylcarbodiimide (DCC), 1-ethyl-3-(3-dimethylaminopropyl)carbodiimide hydrochloride (EDC), 1,1'-carbonyldiimidazole (CDI), propylphosphonic anhydride (T3P) and the like, and the condensing agent is preferably used in 0.1-10 equivalents, more preferably 1-2 equivalents, relative to compound D.

Examples of the additive include 1-hydroxybenzotriazole monohydrate (HOBt H$_2$O), N-hydroxysuccinimide (HOSu) and the like, and the additive is preferably used in 0.1-10 equivalents, more preferably 1-2 equivalents, relative to compound D.

Examples of the solvent include alcohols such as methanol, ethanol and the like; halogenated hydrocarbons such as dichloromethane, chloroform, 1,2-dichloroethane and the like; aromatic hydrocarbons such as toluene, xylene and the like; esters such as methyl acetate, ethyl acetate, isopropyl acetate and the like; ethers such as dioxane, THF, diethyl ether, cyclopentyl methyl ether, DME, ethylene glycol dimethyl ether and the like; polar solvents such as acetonitrile, DMSO, DMF, DMA, NMP, DMI and the like; pyridine; water and the like, preferably polar solvents such as DMF, DMA, NMP, DMI and the like. These are used alone or as a mixture thereof. While the amount of the solvent to be used is not particularly limited, for example, it is used in 0.5-20 v/w relative to compound D.

The reaction is performed at a temperature of preferably between 0° C. and the boiling point of the solvent to be used, more preferably 20° C. and 100° C., generally for 5 min-100 hr.

Compound E can be obtained as a commercially available product.

(2) When Y in compound E is halogen, compound I can be obtained by reacting compound D and compound E without solvent or in a solvent, in the presence of a suitable base as necessary.

Compound E is preferably used in 1-10 equivalents, more preferably 1-2 equivalents, relative to compound D.

Examples of the base include potassium carbonate, potassium hydroxide, sodium hydroxide, potassium tert-butoxide, triethylamine, diisopropylethylamine, N-methylmorpholine, pyridine, 1,8-diazabicyclo[5.4.0]-7-undecene (DBU), 4-dimethylaminopyridine (DMAP) and the like, and the base is preferably used in 1-10 equivalents, more preferably 1-2 equivalents, relative to compound D.

Examples of the solvent include alcohols such as methanol, ethanol and the like; halogenated hydrocarbons such as dichloromethane, chloroform, 1,2-dichloroethane and the like; aromatic hydrocarbons such as toluene, xylene and the like; esters such as methyl acetate, ethyl acetate, isopropyl acetate and the like; ethers such as dioxane, THF, diethyl ether, cyclopentyl methyl ether, DME, ethylene glycol dimethyl ether and the like; polar solvents such as acetonitrile, DMSO, DMF, DMA, NMP, DMI and the like; pyridine; water and the like, preferably methanol, ethanol, dichloromethane, chloroform, 1,2-dichloroethane, toluene, ethyl acetate, acetonitrile, diethyl ether, THF, DME, dioxane, DMF, DMA, NMP, DMI, pyridine, water and the like. These are used alone or as a mixture thereof. While the amount of the solvent to be used is not particularly limited, for example, it is used in 0.5-20 v/w relative to compound D.

The reaction is performed at a temperature of preferably between −30° C. and 150° C., more preferably room temperature and 100° C., generally for 5 min-100 hr.

Compound E can be obtained as a commercially available product, or according to a known method relating to the synthesis of acid chloride conventionally used in the field of organic synthetic chemistry.

In the above-mentioned (1) and (2), when a polar solvent such as DMF, DMA, NMP, DMI and the like is used, compound I can be precipitated from the reaction solution by adding water to the reaction mixture, whereby compound I can be obtained as a solid by a convenient operation.

The resultant products and intermediates in each of the above-mentioned steps can be isolated and purified by subjecting to separation and purification methods conventionally used in the field of organic synthetic chemistry, for example, filtration, extraction, washing, drying, concentration, recrystallization, various chromatographies and the like. The resultant products and intermediates in each step can also be subjected to the next reaction without particular purification.

Some of the intermediates and resultant products obtained in each step may contain stereoisomers such as geometric isomer, optical isomer and the like, tautomer and the like. The intermediates and resultant products in the present invention encompass all possible isomers and mixtures thereof including those mentioned above.

Also, the starting material compounds to be used in each step and the obtained intermediates and resultant products may take the form of salt or solvate.

When a salt of an intermediate or resultant product obtained in each step is desired and the intermediate or resultant product obtained in each step is in the form of a salt, it can be directly purified. When it is obtained in the form of a free form, the intermediate or resultant product obtained in each step is dissolved or suspended in a suitable solvent, an acid or base is added to form a salt and the salt is isolated and purified.

The salt of the starting material compound to be used in each step, intermediate or resultant product obtained in each step encompasses, for example, acid addition salt, metal salt, ammonium salt, organic amine addition salt, amino acid addition salt and the like. Examples of the acid addition salt include inorganic acid salts such as hydrochloride, hydrobromide, nitrate, sulfate, phosphate and the like, organic acid salts such as acetate, oxalate, maleate, fumarate, citrate, benzoate, methanesulfonate and the like, and the like; examples of the metal salt include alkali metal salts such as sodium salt, potassium salt and the like, alkaline earth metal salts such as magnesium salt, calcium salt and the like, aluminum salt, zinc salt and the like; examples of the ammonium salt include salts of ammonium, tetramethylammonium and the like; examples of the organic amine addition salt include addition salts of morpholine, piperidine and the like; and examples of the amino acid addition salt include addition salts of lysine, glycine, phenylalanine, aspartic acid, glutamic acid and the like.

When solvates of the starting material compound to be used in each step, the obtained intermediate and the resultant product are desired, they may be directly obtained by the above-mentioned production method and the like. They can also obtained by mixing the starting material compound to be used in each step, the obtained intermediate or the resultant product with each solvent to form a solvate and subjecting same to isolation and purification.

According to the above-mentioned production method, compound I can be conveniently obtained by a short step than by known methods (for example, WO2005/063743). Also, the production method can efficiently produce compound I with a certain level of quality and with good reproducibility, and is preferable as an industrial production method.

As mentioned above, compound I may be present as a salt thereof or a solvate thereof in addition to a free form, and they can be present in the form of crystals. The crystals of compound I or a salt thereof or a solvate thereof may contain polymorphism and crystal habit. For example, compound I encompasses crystal of compound I, crystal of salt of compound I, crystal of solvate of compound I, crystal of solvate of salt of compound I, and crystal polymorphisms thereof, various crystal habits thereof and the like. More specific examples thereof include anhydride crystal (A crystal) of compound IA, monohydrate crystal (HA crystal) of compound IA, 0.5 ethanolate crystal of compound IA (EA crystal) and the like, which are shown in the below-mentioned Examples and Reference Examples. These crystal forms can be identified, for example, by measuring powder X-ray diffraction, the measured values of powder X-ray diffraction described in the present specification were obtained by a permeation method. The measured values (2θ) of powder X-ray diffraction sometimes may vary within the range of ±0.2°.

While a crystal of the above-mentioned compound IA or a monohydrate thereof is sometimes directly obtained by the above-mentioned method (step 4), for example, it can be produced by the following method.

In the case of an anhydride crystal (A crystal) of compound IA, compound IA is dissolved in isobutyl alcohol at a temperature between 50° C. and 108° C. (boiling point of isobutyl alcohol), preferably between 70° C. and 100° C., and the mixture is cooled with stirring to a temperature between −5° C. and room temperature, whereby A crystal can be obtained in a high yield and with good reproducibility.

Isobutyl alcohol is used in, for example, 10-50 v/w, preferably 20-40 v/w, more preferably 20-30 v/w, relative to compound IA. Compound IA as a starting material may be a compound obtained in the above-mentioned step 4 or, for example, a compound obtained in WO 2005/063743, and is not particularly limited. To maintain quality of a pharmaceutical product, however, a compound having high purity is preferably used. More preferably, for example, a monohydrate of compound IA obtained by the method of the below-mentioned Example 12 and the like may be used. Also, a seed crystal (A crystal) produced separately may be added during cooling, if necessary.

The above-mentioned seed crystal (A crystal) can be obtained by dissolving compound IA obtained according to the above-mentioned step 4 or WO 2005/063743 and the like in isobutyl alcohol at a temperature between 50° C. and 108° C., preferably between 70° C. and 100° C., cooling the mixture with stirring where necessary to a temperature between −5° C. and room temperature. More preferably, a crystal obtained by pulverizing the obtained crystal by a jet mill and the like may be used as a seed crystal.

In the case of a monohydrate crystal (HA crystal) of compound IA, moreover, compound IA is dissolved, for example, in a solvent substantially containing water (for example, DMF-water, ethanol-water, acetone-water and the like) preferably at a temperature between room temperature and the boiling point of the solvent to be used, and the mixture is cooled with stirring to −5° C.—room temperature, whereby HA crystal can be obtained in a high yield and with good reproducibility. To obtain a crystal with high purity, crystallization is more preferably performed from a mixed solvent of acetone-water.

The solvent substantially containing water is used in, for example, 10-50 v/w, preferably 20-40 v/w, more preferably 20-30 v/w, relative to compound IA, which varies depending on the kind of the solvent to be used. If necessary, a seed crystal (HA crystal) produced separately may also be added during cooling.

The above-mentioned seed crystal (HA crystal) can be obtained by dissolving compound IA obtained according to the above-mentioned step 4 or WO 2005/063743 and the like in ethanol-water at a temperature between 50° C. and 100° C., preferably between 70° C. and 90° C., if necessary, cooling the mixture with stirring to a temperature between −5° C. and room temperature. More preferably, a crystal obtained by pulverizing the obtained crystal by a jet mill and the like may be used as a seed crystal.

By the above-mentioned method, a crystal of compound IA or a monohydrate thereof can be efficiently produced with a certain level of quality and with good reproducibility.

As mentioned above, compound IA contains crystal forms of anhydride, monohydrate, ethanolate and the like. A crystal that does not transform into other form even under harsh conditions, for example, high temperature, high humidity and the like, is particularly superior from the aspect of the production of a pharmaceutical product required to be supplied stably. In addition, a crystal superior in oral absorbability is desired as a drug substance of an oral pharmaceutical preparation.

For example, in the case of compound IA, compound IA obtained according to Example 504 of WO 2005/063743 is 0.5 ethanolate (EA crystal) (Reference Example 3), and crystals of monohydrate, anhydride and the like can be obtained with good reproducibility by controlling the crystallization conditions of compound IA. Of these, A crystal and HA crystal can be specifically obtained by the method described in Examples 13-14 with good reproducibility. Of these, A crystal is superior in stability (see Experimental Example 1), and can be preserved with a certain quality for a long term.

Such A crystal and HA crystal show superior oral absorbability (see Experimental Example 2), and are preferable as a drug substance of a pharmaceutical product.

A crystal of compound IA or a monohydrate thereof is granulated by pulverization and the like, if necessary, and can be utilized as an active ingredient of a pharmaceutical preparation, for example, an agent for the treatment and/or prophylaxis of diseases such as Parkinson's disease, sleep disorder, analgesic resistance to opioid, migraine, movement disorder, depression, anxiety disorder and the like.

While a crystal of compound IA or a monohydrate thereof can be administered as it is, it is generally desirably provided as various pharmaceutical preparations. Such pharmaceutical preparations are used for animal or human.

The pharmaceutical preparations can contain, as an active ingredient, a crystal of compound IA or a monohydrate thereof singly or as a mixture with any other active ingredient for the treatment. Such pharmaceutical preparations are produced by mixing the active ingredient with one or more kinds of pharmaceutically acceptable carriers (for example, diluent, solvent, excipient and the like), and according to any method well known in the technical field of the drug formulation study.

As the administration route, one most effective for the treatment is desirably used, which may be oral or, for example, parenteral such as intravenously and the like.

Examples of the administration form include tablet, external preparation, injection and the like.

For example, tablet and the like suitable for oral administration can be produced using excipients such as lactose and the like, disintegrants such as starch and the like, lubricants such as magnesium stearate and the like, binders such as hydroxypropylcellulose and the like, and the like.

Examples of the external preparation and the like suitable for parenteral administration include ointment, cream, liniment, lotion, poultice, plaster, tape and the like. For example, ointment, cream and the like can be produced by dissolving or mixed-dispersing the active ingredient in a base such as white petrolatum and the like. Also, for example, injection and the like can be produced using a diluent, a solvent and the like such as salt solution, glucose solution or a mixture of salt water and glucose solution, and the like.

The dose and administration frequency of a crystal of compound IA or a monohydrate thereof vary depending on the administration form, age, body weight of patients, properties or severity of the symptoms to be treated, and the like. For oral administration, 0.01-1000 mg, preferably 0.05-100 mg, is generally administered per adult in one to several portions per day. For parenteral administration such as intravenous administration and the like, 0.001-1000 mg, preferably 0.01-100 mg, is generally administered per adult once to several times per day. However, these doses and administration frequencies vary depending on the aforementioned various conditions.

The present invention is more specifically explained in the following by referring to Examples and Reference Examples, which are not to be construed as limitative.

The proton nuclear magnetic resonance spectrum ($^1$H NMR) used in the Examples and Reference Examples were measured at 270 MHz or 300 MHz, and exchanging proton may not be observed clearly depending on the compound and measurement conditions. For indication of signal multiplicity, those generally used are employed, wherein br means an apparently broad signal.

Powder X-ray diffraction (permeation method) was measured by pulverizing a sample in an agate mortar, placing an appropriate amount thereof on a sample plate, and measuring diffraction peaks by changing the diffraction angle 2θ from 5° to 40°. The irradiate X ray used was copper Kα ray (CuKα ray), and tube voltage was set to 5 kV, tube electric current was set to 40 mA, step angle was set to 0.017°, and counting time was set to 0.56°/sec. The thermal analysis was performed by placing about 2 mg of a sample on an aluminum cell, and measuring differential scanning calorie (DSC) at a temperature rise rate of 10° C./min.

[Example 1] Production of 4-(furan-2-yl)-2-tert-butylaminothiazol-5-yl=pyridin-2-yl=ketone (Compound C-1)

Compound A-1 (228 mg, 1.0 mmol) obtained in Reference Example 1 and 2-(bromoacetyl)pyridine hydrobromide (281 mg, 1.0 mmol) were dissolved in DMF (2.8 mL) and the mixture was stirred at 40° C. for 9 hr. To the mixture was added water (4.0 mL), and the mixture was extracted with ethyl acetate. The organic layer was washed with saturated brine, dried over anhydrous magnesium sulfate and concentrated under reduced pressure. The residue was purified by silica gel column chromatography (n-hexane:ethyl acetate=9:1) to give compound C-1 (271 mg, 82%).

$^1$H-NMR (CDCl$_3$) δ 1.50 (s, 9H), 6.03 (brs, 1H), 6.51 (dd, J=3.5 Hz, 1.8 Hz, 1H), 7.42 (ddd, J=7.9 Hz, 4.9 Hz, 1.0 Hz, 1H), 7.44 (dd, J=1.8 Hz, 0.7 Hz, 1H), 7.79 (dd, J=3.5 Hz, 0.7 Hz, 1H), 7.86 (td, J=7.9 Hz, 1.8 Hz, 1H), 8.13 (ddd, J=7.9 Hz, 1.0 Hz, 0.9 Hz, 1H), 8.63 (ddd, J=4.9 Hz, 1.8 Hz, 0.9 Hz, 1H). LC/MS ESI(+) m/z 328 [M+H]$^+$.

[Example 2] Production of 4-(furan-2-yl)-2-tert-butylaminothiazol-5-yl=pyridin-3-yl=ketone (Compound C-2)

Compound A-1 (218 mg, 0.96 mmol) obtained in Reference Example 1 and 3-(bromoacetyl)pyridine hydrobromide (278 mg, 1.0 mmol) were dissolved in DMF (2.0 mL) and the mixture was stirred at 40° C. for 10 hr. To the mixture was added water (4.0 mL), and the mixture was extracted with ethyl acetate. The organic layer was washed with saturated brine, dried over anhydrous magnesium sulfate and concentrated under reduced pressure. The residue was purified by silica gel column chromatography (n-hexane: ethyl acetate=7:3) to give compound C-2 (207 mg, 66%).

$^1$H-NMR (CDCl$_3$) δ 1.48 (s, 9H), 6.19 (brs, 1H), 6.31 (dd, J=3.5 Hz, 1.8 Hz, 1H), 6.87 (dd, J=3.5 Hz, 0.6 Hz, 1H), 7.07 (dd, J=1.8 Hz, 0.6 Hz, 1H), 7.26 (dd, J=8.1 Hz, 5.0 Hz, 1H), 7.92 (ddd, J=8.1 Hz, 2.2 Hz, 1.7 Hz, 1H), 8.62 (dd, J=5.0 Hz, 1.7 Hz, 1H), 8.82 (dd, J=2.2 Hz, 0.7 Hz, 1H). LC/MS ESI(+) m/z 328 [M+H]$^+$.

[Example 3] Production of 4-(furan-2-yl)-2-tert-butylaminothiazol-5-yl=tetrahydropyran-4-yl=ketone (Compound C-3)

Compound A-1 (30 mg, 0.13 mmol) obtained in Reference Example 1 and 4-bromoacetyltetrahydropyran (25 mg, 0.12 mmol) were dissolved in DMF (0.5 mL) and the mixture was stirred at 40° C. for 8.5 hr. To the mixture was added water (0.5 mL), and the precipitated solid was collected by filtration. The obtained solid was washed with water (0.5 mL), and dried under reduced pressure to give compound C-3 (37 mg, 92%).

$^1$H-NMR (CDCl$_3$) δ 1.46 (s, 9H), 1.60-1.95 (m, 4H), 3.06 (tt, J=11.1 Hz, 3.9 Hz, 1H), 3.40 (dt, J=11.6 Hz, 2.2 Hz, 2H), 4.02 (ddd, J=11.6 Hz, 4.2 Hz, 2.2 Hz, 2H), 5.81 (brs, 1H), 6.55 (dd, J=3.5 Hz, 1.8 Hz, 1H), 7.48 (dd, J=3.5 Hz, 0.7 Hz, 1H), 7.54 (dd, J=1.8 Hz, 0.7 Hz, 1H). LC/MS ESI(+) m/z 335 [M+H]$^+$.

[Example 4] Production of 4-(furan-2-yl)-2-(1-methyl-1-phenylethyl)aminothiazol-5-yl=tetrahydropyran-4-yl=ketone (Compound C-4)

Compound A-2 (580 mg, 2.0 mmol) obtained in Reference Example 2 and 4-bromoacetyltetrahydropyran (416 mg, 2.0 mmol) were dissolved in DMF (2.0 mL) and the mixture was stirred at 40° C. for 8 hr. Under ice-cooling, the mixture was neutralized with saturated aqueous sodium hydrogen carbonate solution, and the mixture was extracted with ethyl acetate. The organic layer was washed with saturated brine, dried over anhydrous magnesium sulfate and concentrated under reduced pressure. The residue was purified by silica gel column chromatography (n-hexane: ethyl acetate=4:1-1:1) to give compound C-4 (690 mg, 87%).

$^1$H-NMR (CDCl$_3$) δ 1.53-1.83 (m, 4H), 1.76 (s, 6H), 2.79 (tt, J=12.9 Hz, 3.7 Hz, 1H), 3.29 (dt, J=11.6 Hz, 2.3 Hz, 2H), 3.94 (ddd, J=11.6 Hz, 3.6 Hz, 2.3 Hz, 2H), 6.54 (dd, J=3.5 Hz, 1.7 Hz, 1H), 6.76 (brs, 1H), 7.28-7.42 (m, 3H), 7.44-7.51 (m, 3H), 7.54 (dd, J=1.7 Hz, 0.8 Hz, 1H).

[Example 5] Production of 2-amino-4-(furan-2-yl)thiazol-5-yl=pyridin-2-yl=ketone (Compound D-1)

Compound C-1 (263 mg, 0.80 mmol) obtained in Example 1 was dissolved in concentrated hydrochloric acid (2.6 mL), and the mixture was stirred at 80° C. for 3.5 hr. Under ice-cooling, the mixture was neutralized with saturated aqueous sodium hydrogen carbonate solution, and the precipitated solid was collected by filtration. The obtained solid was washed with water (6.0 mL), and dried under reduced pressure to give compound D-1 (140 mg, 64%).

$^1$H-NMR (DMSO-d$_6$) δ 6.56 (dd, J=3.5 Hz, 1.7 Hz, 1H), 7.44 (dd, J=3.5 Hz, 0.7 Hz, 1H), 7.53-7.61 (m, 2H), 7.94-8.08 (m, 2H), 8.05 (brs, 2H), 8.57 (ddd, J=5.0 Hz, 1.7 Hz, 0.9 Hz, 1H). LC/MS ESI(+) m/z 272 [M+H]$^+$.

[Example 6] Production of 2-amino-4-(furan-2-yl)thiazol-5-yl=pyridin-3-yl=ketone (Compound D-2)

Compound C-2 (207 mg, 0.63 mmol) obtained in Example 2 was dissolved in concentrated hydrochloric acid (2.0 mL), and the mixture was stirred at 80° C. for 3.5 hr. Under ice-cooling, the mixture was neutralized with saturated aqueous sodium hydrogen carbonate solution, and the precipitated solid was collected by filtration. The obtained solid was washed with water (3.0 mL), and dried under reduced pressure to give compound D-2 (127 mg, 74%).

$^1$H-NMR (DMSO-d$_6$) δ 6.40 (dd, J=3.5 Hz, 1.8 Hz, 1H), 6.80 (dd, J=3.5 Hz, 0.4 Hz, 1H), 7.28 (dd, J=1.8 Hz, 0.4 Hz, 1H), 7.35 (ddd, J=8.0 Hz, 4.9 Hz, 0.6 Hz, 1H), 7.85 (ddd, J=8.0 Hz, 2.2 Hz, 1.8 Hz, 1H), 8.15 (brs, 2H), 8.60 (dd, J=4.9 Hz, 1.8 Hz, 1H), 8.63 (dd, J=2.2 Hz, 0.6 Hz, 1H). LC/MS ESI(+) m/z 272 [M+H]$^+$.

[Example 7] Production of 2-amino-4-(furan-2-yl)thiazol-5-yl=tetrahydropyran-4-yl=ketone (Compound D-3)—(1)

Compound C-3 (30 mg, 0.09 mmol) obtained in Example 3 was dissolved in concentrated hydrochloric acid (1.0 mL), and the mixture was stirred at 80° C. for 1.5 hr. Under ice-cooling, the mixture was neutralized with saturated aqueous sodium hydrogen carbonate solution, and the precipitated solid was collected by filtration. The obtained solid was washed with water (0.5 mL), and dried under reduced pressure to give compound D-3 (22 mg, 87%).

$^1$H-NMR (CDCl$_3$) δ 1.68-1.95 (m, 4H), 2.99 (tt, J=11.0 Hz, 3.9 Hz, 1H), 3.40 (dt, J=11.6 Hz, 2.4 Hz, 2H), 4.02 (ddd, J=11.6 Hz, 4.0 Hz, 2.4 Hz, 2H), 5.58 (brs, 2H), 6.56 (dd, J=3.5 Hz, 1.8 Hz, 1H), 7.55 (d, J=3.5 Hz, 1H), 7.56 (d, J=1.8 Hz, 1H). LC/MS ESI(+) m/z 279 [M+H]$^+$.

[Example 8] Production of Compound D-3—(2)

A mixture of compound C-3 (80 g, 0.24 mol) obtained in Example 3, concentrated hydrochloric acid (200 mL) and water (200 mL) was stirred at 95-108° C. for 4 hr while evaporating low boiling substances. To the mixture was added dropwise at 95° C. warm water (80 mL) at 90° C., and the mixture was stirred at the same temperature for 30 min and then at 85° C. for 30 min, and cooled to 50° C. Methanol (240 mL) was added dropwise. The mixture was adjusted to pH 9.5 with aqueous sodium hydroxide solution (8 mol/L), cooled to 5° C., and the precipitated solid was collected by filtration. The obtained solid was washed with cold 10% aqueous methanol solution, and dried under reduced pressure to give compound D-3 (61 g, 92%). [Example 9] Production of compound D-3—(3)

Compound C-4 (50 mg, 0.13 mmol) obtained in Example 4 was dissolved in trifluoroacetic acid (0.5 mL), and the mixture was stirred at 40° C. for 3 hr. Under ice-cooling, the mixture was neutralized with saturated aqueous sodium hydrogen carbonate solution, and the mixture was extracted with ethyl acetate. The organic layer was washed with saturated brine, dried over anhydrous magnesium sulfate and concentrated under reduced pressure. The residue was purified by thin layer silica gel column chromatography (n-hexane:ethyl acetate=1:1) to give compound D-3 (21 mg, 59%).

[Example 10] Production of N-[4-(furan-2-yl)-5-(tetrahydrofuran-4-carbonyl)thiazol-2-yl]-6-methyl-pyridine-3-carboxamide (Compound IA) monohydrate A mixture of compound D-3 (500 g, 1.80 mol) obtained in Example 7, activated carbon (C2, 25 g) and DMF (1.3 L)

was stirred at 60° C. for 1 hr. The activated carbon was filtered off at the same temperature, to the filtrate were added 6-methylnicotinic acid (419 g, 3.06 mol), CDI (495 g, 3.06 mol) and DMF (875 mL) at room temperature, and the mixture was stirred at 90° C. for 3 hr. The mixture was cooled to 60° C., activated carbon (C2, 50 g) and DMF (250 mL) were added, and the mixture was stirred at the same temperature for 1 hr. The activated carbon was filtered off at the same temperature, and washed with DMF (500 mL) at the same temperature. The filtrate was cooled to 40° C., water (1.5 L) was added dropwise over 30 min with stirring at the same temperature, and the mixture was stirred at the same temperature for 30 min. Water (1.5 L) was further added dropwise. The mixture was cooled to 5° C., stirred for 6 hr, and the precipitated solid was collected by filtration. The obtained solid was washed with cold 50% aqueous methanol solution (1.0 L), and dried under reduced pressure to give compound IA monohydrate (619 g, yield 84%).

[Example 11] Production of Compound IA Monohydrate Crystal (HA Crystal)

Figure 1:
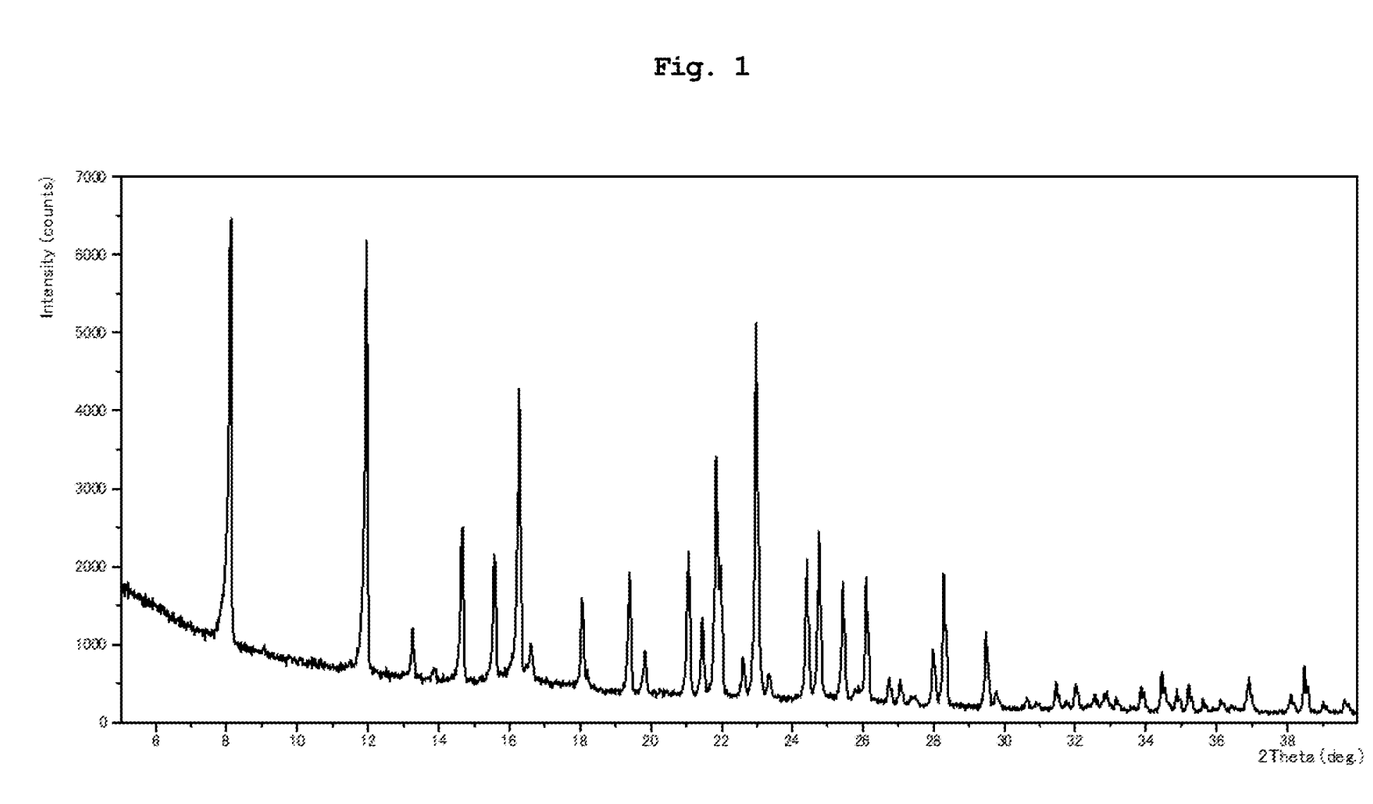
FIG. 1 shows a powder X-ray diffraction pattern of a crystal of compound IA monohydrate (HA crystal), wherein the vertical axis shows diffraction intensity (Counts/sec), and the horizontal axis shows diffraction angle (2θ, °).

Compound IA monohydrate (80 g, 0.19 mol) obtained in Example 10 was dissolved in a mixed solvent of water (0.56 L) and acetone (2.24 L) at 55° C., activated carbon (C2, 8 g) was added and the mixture was stirred for 30 min. The activated carbon was filtered off at the same temperature, and washed with warm 80% aqueous acetone solution (0.16 L). HA crystal (0.40 g) obtained in Example 13 was added as a seed crystal while stirring the filtrate at 40° C., and the mixture was cooled to 0° C. over 3 hr, and stirred at the same temperature for 15 hr. The precipitated solid was collected by filtration, the obtained solid was washed with cold 50% aqueous acetone solution (0.10 L), and dried under reduced pressure at 45° C. for 48 hr to give compound IA HA crystal (72 g, yield 90%).
powder X-ray diffraction measurement results: peaks at diffraction angles (2θ)=8.1, 12.0, 14.7, 16.3, 21.1, 21.8, 23.0, 24.4, 24.7, 28.3° (see FIG. 1).
thermal analysis (DSC) measurement results: endothermic peaks at about 133° C. and about 209° C.

[Example 12] Production of Compound IA Anhydride Crystal (A Crystal)

Figure 2:
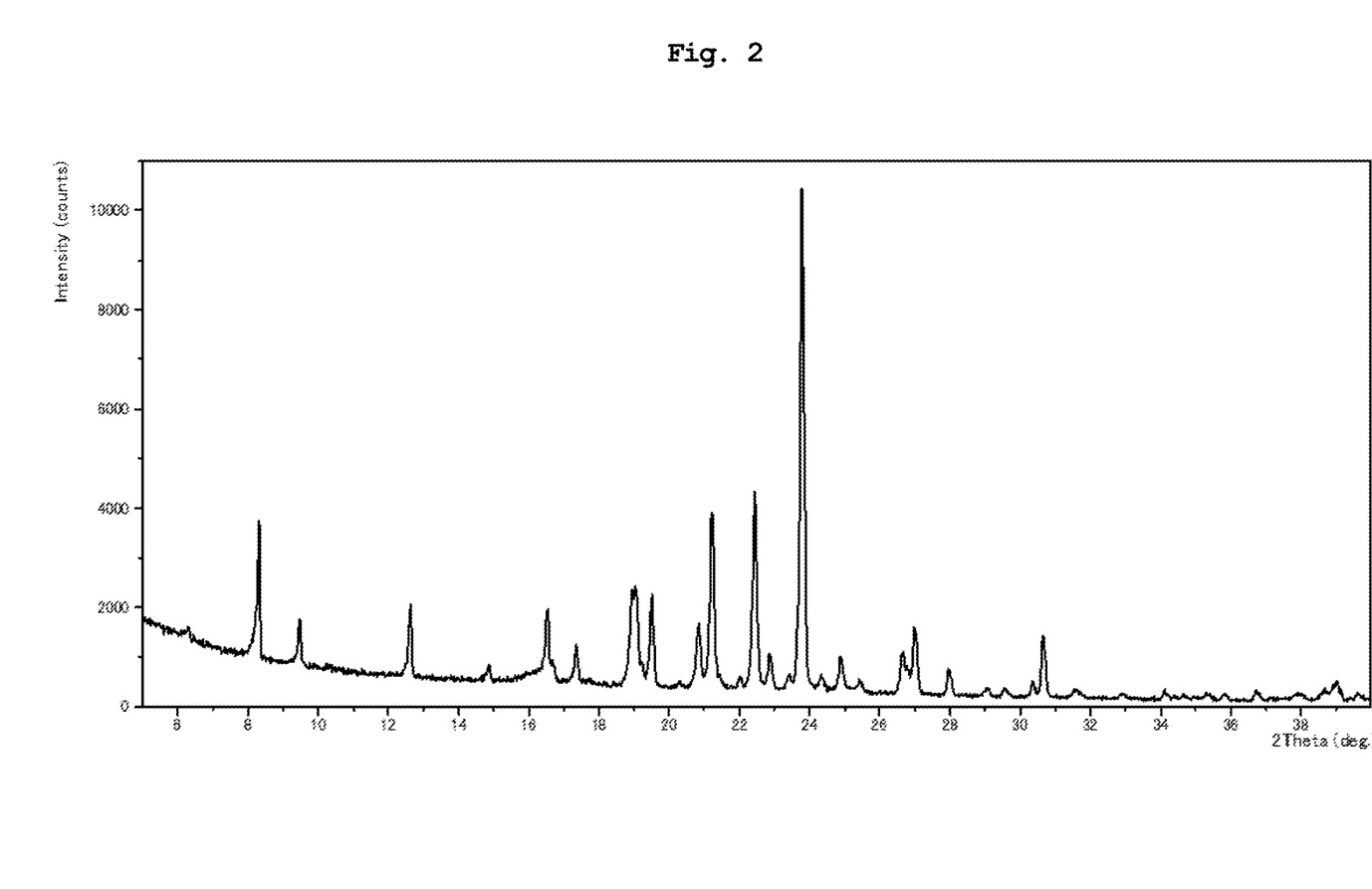
FIG. 2 shows a powder X-ray diffraction pattern of a crystal of compound IA anhydride (A crystal), wherein the vertical axis shows diffraction intensity (Counts/sec), and the horizontal axis shows diffraction angle (2θ, °).

Compound IA monohydrate (300 g, 0.72 mol) obtained in Example 10 was dissolved in isobutyl alcohol (8.1 L) at 80° C., activated carbon (C2, 30 g) was added and the mixture was stirred for 30 min. The activated carbon was filtered off at the same temperature, and washed with warm isobutyl alcohol (0.6 L). The A crystal (1.5 g) obtained in Example 14 was added as a seed crystal to the filtrate while stirring the filtrate at 70° C. The mixture was further stirred at the same temperature for 1 hr, cooled to 5° C. over 6 hr, and further stirred at the same temperature for 18 hr. The precipitated solid was collected by filtration, the obtained solid was washed with cold isobutyl alcohol (0.60 L), and dried under reduced pressure at 50° C. to give A crystal (262 g, yield 93%).
powder X-ray diffraction measurement results: peaks at diffraction angles (2θ)=8.3, 12.6, 16.5, 19.1, 19.5, 20.8, 21.2, 22.4, 23.8, 27.0° (see FIG. 2).
thermal analysis (DSC) measurement results: endothermic peak at about 210° C.

[Example 13] Production of Seed Crystal of HA Crystal

Compound IA monohydrate (550 g, 1.38 mol) obtained in Example 10 was dissolved in a mixed solvent of water (1.1 L) and ethanol (9.9 L) at 80° C. The solution was added dropwise to water (1.1 L) over 20 min, and the mixture was stirred at 20° C. for 1.5 hr, and further at 0° C. for 2.5 hr. The precipitated solid was collected by filtration, the obtained solid was washed with a mixed solvent (400 mL) of cold water (320 mL) and cold ethanol (80 mL), and dried under reduced pressure at 55° C. to give HA crystal (525 g, yield 95%).
The HA crystal (515 g) was pulverized by a jet mill and the pulverized crystal was used as a seed crystal.
powder X-ray diffraction measurement results: peaks at diffraction angles (2θ)=8.1, 12.0, 14.7, 16.3, 21.1, 21.8, 23.0, 24.4, 24.7, 28.3°.

[Example 14] Production of Seed Crystal of a Crystal

Compound IA monohydrate (40 g, 96 mmol) obtained in Example 10 was dissolved in isobutyl alcohol (1.2 L) at 80° C., and the solution was cooled to 5° C. over 8 hr. The solution was further stirred at the same temperature for 16 hr, the precipitated solid was collected by filtration, the obtained solid was washed with cold isobutyl alcohol (80 mL), and dried under reduced pressure at 50° C. to give A crystal (37 g, yield 95%). The A crystal (34 g) was pulverized by a jet mill. The pulverized crystal was used as a seed crystal.
powder X-ray diffraction measurement results: peaks at diffraction angles (2θ)=8.3, 12.6, 16.5, 19.1, 19.5, 20.8, 21.2, 22.4, 23.8, 27.0°.

(Reference Example 1) Production of 1-tert-butyl-3-(furan-2-yl) carbonylthiourea (Compound A-1)

Sodium thiocyanate (0.91 g, 11 mmol) was suspended in THF (5.0 mL), 2-furoyl chloride (1.0 mL, 10 mmol) was added at 40° C., and the mixture was stirred for 10 min. After ice-cooling, tert-butylamine (1.1 mL, 11 mmol) was added to the mixture, and the mixture was stirred at 40° C. for 30 min. Water (10.0 mL) was added to the mixture, and the mixture was stirred at room temperature for 30 min. The precipitated solid was collected by filtration, washed with water (5.0 mL), and dried under reduced pressure to give compound A-1 (1.86 g, 81%).
$^1$H-NMR (CDCl$_3$) δ 1.59 (s, 9H), 6.59 (dd, J=3.6 Hz, 1.7 Hz, 1H), 7.29 (dd, J=3.6 Hz, 0.8 Hz, 1H), 7.57 (dd, J=1.7 Hz, 0.8 Hz, 1H), 8.86 (brs, 1H), 10.62 (brs, 1H). LC/MS (ESI(+)) m/z 227 [M+H]$^+$.

(Reference Example 2) Production of 1-(1-methyl-1-phenylethyl)-3-(furan-2-yl)carbonylthiourea (Compound A-2)

Sodium thiocyanate (922 mg, 11 mmol) was suspended in THF (5.0 mL), 2-furoyl chloride (1.0 mL, 10 mmol) was added at 40° C., and the mixture was stirred for 10 min. After ice-cooling, 1-methyl-1-phenylethylamine (1.5 mL, 11 mmol) was added to the mixture, and the mixture was stirred at room temperature for 1.5 hr. Water (10.0 mL) was added to the mixture, and the mixture was extracted with ethyl acetate. The organic layer was washed with saturated brine, dried over anhydrous magnesium sulfate, and concentrated under reduced pressure. Ethanol (3.0 mL) was added to the obtained residue and the mixture was stirred, and the precipitated solid was collected by filtration, and dried under reduced pressure to give compound A-2 (1.85 g, 63%).

$^1$H-NMR (CDCl$_3$) δ 1.90 (s, 6H), 6.60 (dd, J=3.6 Hz, 1.7 Hz, 1H), 7.20-7.42 (m, 5H), 7.33 (dd, J=3.6 Hz, 0.8 Hz, 1H), 7.57 (dd, J=1.7 Hz, 0.8 Hz, 1H), 8.91 (brs, 1H), 11.05 (brs, 1H).

(Reference Example 3) Production of Compound IA by the Method Described in WO2005/063743 (Production of Compound IA 0.5 Ethanolate (EA Crystal))

Figure 3:
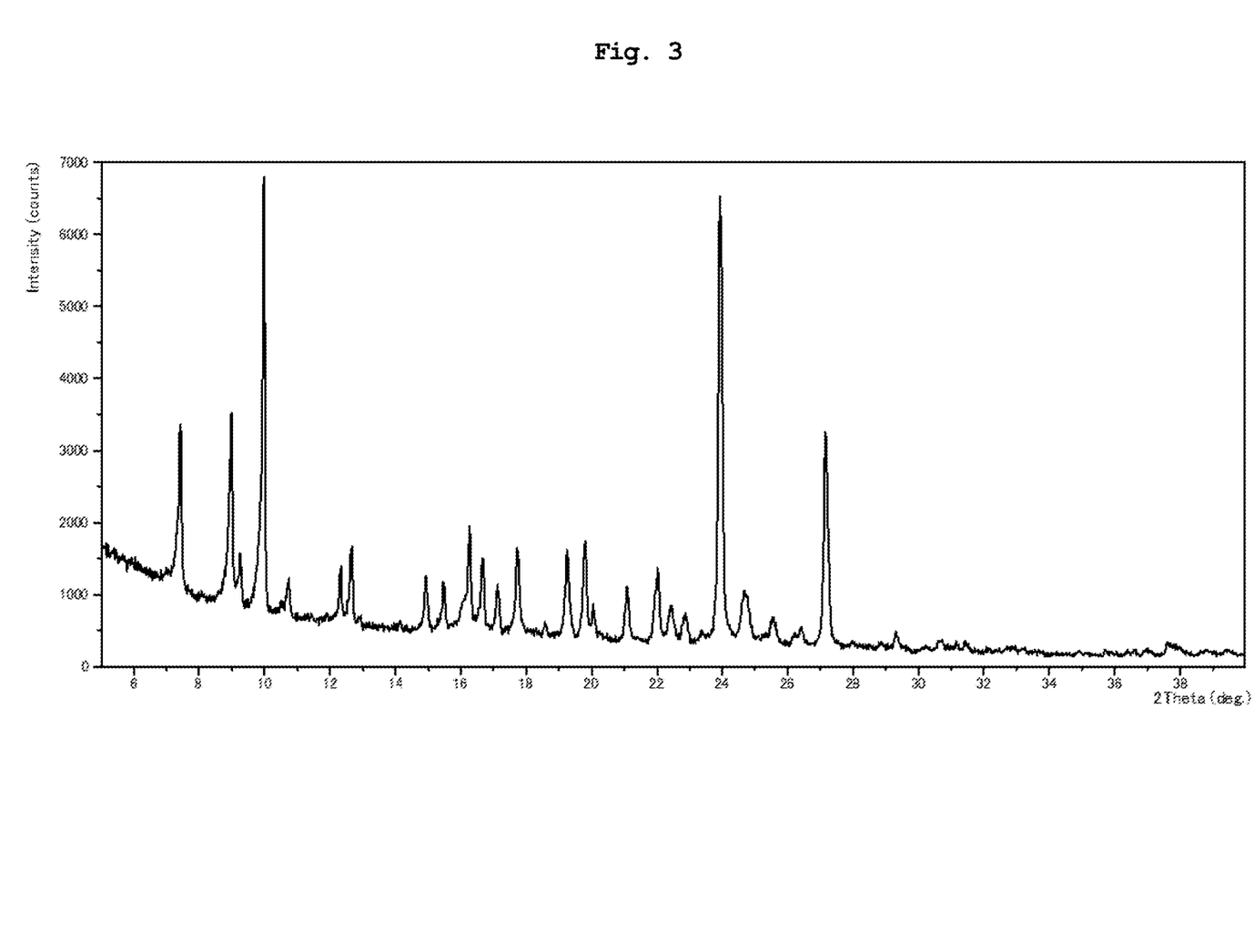
FIG. 3 shows a powder X-ray diffraction pattern of a crystal of compound IA 0.5 ethanolate (EA crystal), wherein the vertical axis shows diffraction intensity (Counts/sec), and the horizontal axis shows diffraction angle (2θ, °).

In the same manner as in Example 504 of WO 2005/063743, compound IA was obtained as a pale-brown solid. The obtained solid was confirmed to be compound IA 0.5 ethanolate crystal (EA crystal) from various spectrum data ($^1$H NMR spectrum, powder X-ray diffraction, thermal analysis, elemental analysis and the like).

powder X-ray diffraction measurement results: peaks at diffraction angles (2θ)=7.4, 9.0, 10.0, 12.7, 16.3, 17.7, 19.3, 19.8, 23.9, 27.2° (see FIG. 3).

thermal analysis (DSC) measurement results: endothermic peaks at about 154° C., about 198° C. and about 208° C.

Experimental Example 1: Stability Test

The A crystal obtained in Example 12 was preserved under the conditions of 40° C./75% RH (relative humidity) and 40° C./90% RH (relative humidity) for 6 months each, and powder X-ray diffraction was measured. When compared with the diffraction pattern at the time of the start of the preservation, the diffraction pattern did not show any change under the both conditions. It was confirmed that A crystal is stable even after preservation for a long term under humidified conditions of 40° C./75% RH (relative humidity) and 40° C./90% RH (relative humidity).

The HA crystal obtained in Example 11 was preserved for 2 weeks at 60° C., and then powder X-ray diffraction was measured. When compared with the diffraction pattern at the time of the start of the preservation, the diffraction pattern after preservation was confirmed to show a diffraction peak characteristic of A crystal. That is, a part of HA crystal is considered to undergo crystal transition to A crystal at 60° C.

Experimental Example 2: Absorbability Test

HA crystal and A crystal obtained in Examples 11 and 12 were orally administered to male rats respectively, and plasma kinetics of compound IA were evaluated. The results are shown in Table 1 and Table 2.

TABLE 1

| Plasma kinetics of HA crystal | | | | | |
|---|---|---|---|---|---|
| dose | $t_{max}$ (h) | $C_{max}$ (ng/mL) | $t_{1/2}$ (h) | AUC$_{0\to\infty}$ (ng · h/mL) | BA (%) |
| 1 mg/kg | 1.33 ± 0.58 | 1500 ± 100 | 2.08 ± 0.13 | 5930 | 59.5 |
| 10 mg/kg | 2.00 ± 0.00 | 10900 ± 800 | 3.43 ± 1.14 | 56600 | 56.8 |

TABLE 2

| Plasma kinetics of A crystal | | | | | |
|---|---|---|---|---|---|
| dose | $t_{max}$ (h) | $C_{max}$ (ng/mL) | $t_{1/2}$ (h) | AUC$_{0\to\infty}$ (ng · h/mL) | BA (%) |
| 1 mg/kg | 1.00 ± 0.00 | 1410 ± 270 | 2.26 ± 0.26 | 5350 | 53.7 |
| 10 mg/kg | 1.67 ± 0.58 | 11400 ± 1400 | 1.77 ± 0.09 | 51000 | 51.2 |

As a result, both HA crystal and A crystal showed good bioavailability, and they were confirmed to have superior properties as pharmaceutical products.

The plasma concentration increased more rapidly in A crystal than in HA crystal.

INDUSTRIAL APPLICABILITY

According to the present invention, a production method of a compound represented by the formula (I), which has an adenosine A$_{2A}$ receptor antagonistic action and is useful as a therapeutic agent for, for example, Parkinson's disease, sleep disorder, analgesic resistance to opioid, migraine, movement disorder, depression, anxiety disorder and the like, a crystal of a compound represented by the formula (IA) or a monohydrate thereof and a production method thereof and the like can be provided. The production methods of the present invention are useful as industrial production methods of a drug substance of a pharmaceutical product. Also, a crystal form of a compound represented by the formula (IA) or a monohydrate thereof of the present invention is useful as a drug substance of a pharmaceutical product.

This application is a divisional of application Ser. No. 15/541,857 filed Jul. 6, 2017, which is a national phase of PCT Application No. PCT/JP2016/051197 filed Jan. 8, 2016, which in turn is based on patent application No. 2015-2964 filed Jan. 9, 2015 in Japan, the contents of which are incorporated in full herein.

The invention claimed is:

1. An anhydrous crystal of a compound represented by formula (IA)

(IA)

said anhydrous crystal having at least one peak at 8.3°, 20.8°, 21.2° or 22.4° for the angles of diffraction (2θ±0.2°) as determined by powder X-ray diffraction.

2. The crystal according to claim 1, which has peaks at 8.3° and 19.1° for the angles of diffraction (2θ±0.2°) as determined by powder X-ray diffraction.

3. The crystal according to claim 1, which has peaks at 21.2°, 23.8° and 27.0° for the angles of diffraction (2θ±0.2°) as determined by powder X-ray diffraction.

4. A production method of the crystal described in claim 1, comprising a step of crystallizing a compound represented by the formula (IA) from isobutyl alcohol.

5. The crystal according to claim 2, which has peaks at 21.2°, 23.8° and 27.0° for the angles of diffraction (2θ±0.2°) as determined by powder X-ray diffraction.

6. A production method of the crystal described in claim 2, comprising a step of crystallizing a compound represented by the formula (IA) from isobutyl alcohol.

7. A production method of the crystal described in claim 3, comprising a step of crystallizing a compound represented by the formula (IA) from isobutyl alcohol.

8. A production method of the crystal described in claim 5, comprising a step of crystallizing a compound represented by the formula (IA) from isobutyl alcohol.

* * * * *

UNITED STATES PATENT AND TRADEMARK OFFICE
CERTIFICATE OF CORRECTION

| | | |
|---|---|---|
| PATENT NO. | : 10,618,894 B2 | Page 1 of 2 |
| APPLICATION NO. | : 16/246988 | |
| DATED | : April 14, 2020 | |
| INVENTOR(S) | : Takamasa Sugita et al. | |

It is certified that error appears in the above-identified patent and that said Letters Patent is hereby corrected as shown below:

On the Title Page

Item [56] REFERENCES CITED:
Other Publications, "Pseudopolynnorph" should read --Pseudopolymorph--;
    "Crystal Growth &amp; design" should read --Crystal Growth & Design--;
Other Publications, Page 2, "-5'thiazolylcarbonyl)-" should read -- -5'-thiazolylcarbonyl)- --;
Other Publications, Page 2, "thizone-5-yl" should read --thiazone-5-yl--; and
Other Publications, Page 2, "2-Aminothizoles" should read --2-Aminothiazoles--.

In the Specification

Column 6:
Line 64, "$R^2$, $R^{2}$" should read --$R^1$, $R^2$--.

Column 9:
Line 49, "triazolyl," should read --thiazolyl,--.

Column 11:
Line 57, "thereof." should read --thereof. Preferred--;
Line 58, "¶Preferred" should read --Preferred--; and
Line 66, "Step 2 Compound C" should read --Step 2¶Compound C--.

Column 15:
Line 44, "also obtained" should read --also be obtained--; and
Line 49, "conveniently" should read --more conveniently--.

Column 16:
Line 3, "diffraction," should read --diffraction;--.

Signed and Sealed this
Sixteenth Day of November, 2021

Drew Hirshfeld
*Performing the Functions and Duties of the*
*Under Secretary of Commerce for Intellectual Property and*
*Director of the United States Patent and Trademark Office*

Column 17:
Line 38, "animal or human." should read --animals or humans.--.

Column 20:
Line 47, "92%). [Example 9]" should read --92%).--; and
Line 48, "Production" should read --¶[Example 9] Production--.

Column 22:
Line 16, "of a" should read --of A--.

In the Claims

Column 24:
Line 63, "(20±0.2°)" should read --(2θ±0.2°)--.

Column 25:
Line 2, "(20±0.2°)" should read --(2θ±0.2°)--.